United States Patent [19]

Cork

[11] Patent Number: 4,873,875
[45] Date of Patent: Oct. 17, 1989

[54] SYSTEM FOR OPTICALLY INTERROGATING LIQUID SAMPLES AND FOR WITHDRAWING SELECTED SAMPLE PORTIONS

[75] Inventor: William H. Cork, Brecksville, Ohio

[73] Assignee: Prism Technology, Inc., Brecksville, Ohio

[21] Appl. No.: 879,588

[22] Filed: Jun. 27, 1986

[51] Int. Cl.[4] .................. G01N 1/14; G01N 21/17
[52] U.S. Cl. .................. 73/863.01; 73/864.23; 250/577
[58] Field of Search ............ 73/864, 864.01, 864.11, 73/864.23, 864.24, 864.25, 864.31, 863.01, 293; 250/577; 210/744, 745; 422/100

[56] References Cited

U.S. PATENT DOCUMENTS

| | | | |
|---|---|---|---|
| 2,982,170 | 5/1961 | Wyss | 73/61.4 |
| 3,443,439 | 5/1969 | Cruz | 73/864.23 |
| 3,581,574 | 6/1971 | Smith | 73/864.23 |
| 3,596,673 | 8/1971 | Laucournet | 250/577 |
| 4,158,035 | 6/1979 | Haase et al. | 73/864.23 |
| 4,252,438 | 2/1981 | Haina et al. | 250/577 |
| 4,311,667 | 1/1982 | Gocho | 73/864.24 |
| 4,420,254 | 12/1983 | Smeaton | 73/864.11 |
| 4,487,836 | 12/1984 | Takayanagi et al. | 73/863.01 |
| 4,555,957 | 12/1985 | Frankel et al. | 73/864.25 |
| 4,586,546 | 5/1986 | Mezei et al. | 73/864.24 |

FOREIGN PATENT DOCUMENTS

| | | | |
|---|---|---|---|
| 0039185 | 4/1978 | Japan | 73/863.01 |
| 0071897 | 6/1978 | Japan | 73/864.24 |
| 0108754 | 6/1985 | Japan | 422/100 |
| 2069974 | 9/1981 | United Kingdom | 73/864.23 |

*Primary Examiner*—Tom Noland
*Assistant Examiner*—Robert R. Raevis
*Attorney, Agent, or Firm*—David A. Burge

[57] ABSTRACT

A system for interrogating non-homogeneous liquid samples to locate regions of interest within the samples, and to extract liquid from the regions of interest. The system of the invention is particularly well adapted for use in locating and in thoroughly removing liquid from regions of interest that include even extremely thin, film-like, horizontally extending layers of interest that typically are in the range of about 10 to 50 microns in thickness. The system utilizes a polarized beam of collimated laser light that is projected along a horizontal travel path, that is transmitted through a sample, and that is detected to enable characteristics of the transmitted light beam that have been affected by characteristics of the interrogated sample portions to be studied. By this arrangement, a centrifuged sample of liquid that differs in content at different height levels can be interrogated to locate levels within the sample where one or more layers of components of interest reside that are to be withdrawn from the sample. Withdrawal of liquid components from each such layer is effected by inserting a pipette into the sample to a level where the components reside, and by withdrawing the components through the pipette.

5 Claims, 5 Drawing Sheets

SYSTEM FOR OPTICALLY INTERROGATING LIQUID SAMPLES AND FOR WITHDRAWING SELECTED SAMPLE PORTIONS

BACKGROUND OF THE INVENTION

1. Field of the Invention

The present invention relates to a system for optically interrogating non-homogeneous samples of liquid by scanning the samples with a beam of light to locate regions of interest, and for withdrawing liquid from the regions of interest. Features of the present invention are especially useful in interrogating centrifuged samples of liquids that have distinct layers of components at different height levels within test tubes, wherein it is desired to remove sample portions that comprise one or more of the layers.

2. Prior Art

Inspection and detection systems of many forms have been proposed that utilize visible and/or invisible electromagnetic radiation as a projected medium for interrogating objects including samples of liquid, with transmission, reflection, refraction or other characteristics being detected to determine information about the interrogated samples. It has been proposed, for example, to scan a solid object with a beam of laser light, and to detect the intensity of the reflected light, with sensed differences in reflected light intensity being indicative of the locations of physical features of the object that are known to exist within a designated area of investigation.

Automated systems of various types have been proposed for effecting sequential movements of container carried samples of liquid to and from test stations for examination, treatment, and/or withdrawal of portions of the samples from their containers. For example, apparatus for effecting automated testing of samples of body fluids such as blood and urine are known, with the apparatus typically having capabilities to extract sample portions and to subject the extracted liquids to various types of tests and measurements. However, these automated systems are intended for use with samples that are substantially homogeneous in character, not for use with non-homogeneous samples such as centrifuged samples of liquid that have layers that differ in consistency.

Despite a plethora of proposals that have been made in efforts to provide a variety of automated inspection, detection, and sampling systems, a technique that continues to be used as a mainstay in laboratories where thin layers of centrifuged samples of liquid must be withdrawn, is manual precision pipetting. This technique includes the steps of inserting pipettes into container-carried samples of centrifuged liquid, with the insertion of the pipettes being guided by eye and hand coordination, and with the precision of the withdrawal of selected sample portions being determined by the, skill, care and luck of the laboratory technician who performs these manual tasks. In situations where centrifuged samples have extremely thin layers of liquid that are to be withdrawn, with these very thin layers of interest typically being in the range of about 10 to 50 microns in thickness, the use of manual precision pipetting techniques by even the most skilled and experienced technicians achieve results that vary widely from one pipetting operation to the next. The results vary both in the percentages of the desired components that escape extraction, and in the percentages of unwanted liquid components are found to be included in the liquid that has been extracted. A nearly perfect extraction (i.e., an extraction that succeeds in withdrawing substantially all of the desired components with substantially no accompanying withdrawal of unwanted components) is rarely achieved.

Thus, a long-standing need has remained unfulfilled for a method and apparatus that will enable selected portions of liquid samples to be located and extracted accurately and effectively, sample after sample. The need has been especially prevalent where centrifuged samples of liquid contain extremely thin layers of liquid at various height levels that must be located and extracted with extreme accuracy, with exacting degrees of control being required both in positioning pipettes that are used to withdraw liquid from the thin layers of interest, and in conducting thorough extractions of components that comprise the layers of interest but without causing the accompanying extraction of undesired components.

SUMMARY OF THE INVENTION

The foregoing and other needs and drawbacks of the prior art are addressed by the present invention through the provision of methods and apparatus for optically interrogating liquid samples to precisely locate regions of interest within the samples, and for precisely withdrawing desired quantities of liquid from the regions of interest.

In accordance with features of the present invention, light from a source such as a laser is projected along a predetermined path of travel toward a sample of liquid. Light that has been transmitted through the sample is detected to study characteristics of the transmitted light beam that have-been affected by characteristics of the interrogated sample portions. Preferably, a liquid sample is held by a transparent container such as a vertically oriented test tube, and a polarized beam of collimated laser light is projected along a substantially horizontal travel path for transmission through the sample. Light transmitted through the sample is received by a light sensitive detector that monitors and records variations in light intensity that are detected as relative vertical movement is effected between the sample and the travel path of the beam. By this arrangement, a determination is made as to how the transmission of the beam of light is affected by portions of the sample at different height levels within the container. Thus, a centrifuged sample of liquid that differs in content at different height levels can be interrogated to locate levels within the sample where one or more layers of components of interest reside that are to be withdrawn from the sample. Withdrawal of components of interest from each such layer is effected by inserting a pipette into the sample to a level where the components reside, and by withdrawing the components through the pipette.

In preferred practice, features of the present invention are practiced utilizing an automated apparatus that is controlled by a microprocessor system. Basic characteristics of the samples that are to be examined are ascertained so that the apparatus can be preset to detect characteristics that mark locations of levels of interest, with the apparatus functioning to accurately effect automated withdrawal of calculated volumes of desired components from the samples. A microprocessor control system preferably performs such functions as comparing sensed values with predetermined values to locate levels of interest within interrogated samples. The control system likewise effects precise relative movements of sample containers, beam travel paths and/or pipettes to implement automated sample scanning, extraction and collection procedures. Additionally, the control system determines the character and extent of the pipette suction action that is employed so that desired sample portions are extracted without causing undue disturbance to adjacent sample portions (i.e., to assure that unwanted sample portions are not caused to be drawn into the pipettes).

BRIEF DESCRIPTION OF THE DRAWINGS

These and other features, and a fuller understanding of the invention may be had by referring to the following description and claims taken in conjunction with the accompanying drawings, wherein:

FIG. 1 is a perspective view of an apparatus that embodies features of the preferred practice of the present invention, with the apparatus including a container positioning stage that is movable relative to a support structure in substantially horizontal and vertical directions that are indicated by "X" and "Y" axes, respectively, and a pipette positioning stage that is movable relative to the support structure and to the container positioning stage in a substantially horizontal direction that is indicated by a "Z" axis, with the container positioning stage being centered along its leftwardly and rightwardly extending range of X axis movement, and being near the lower end of its upwardly and downwardly extending range of Y axis movement, and with the pipette positioning stage being near the forward end of its forwardly and rearwardly extending range of Z axis movement;

DESCRIPTION OF THE PREFERRED EMBODIMENT

1. Brief Overview of Apparatus

Figure 1:
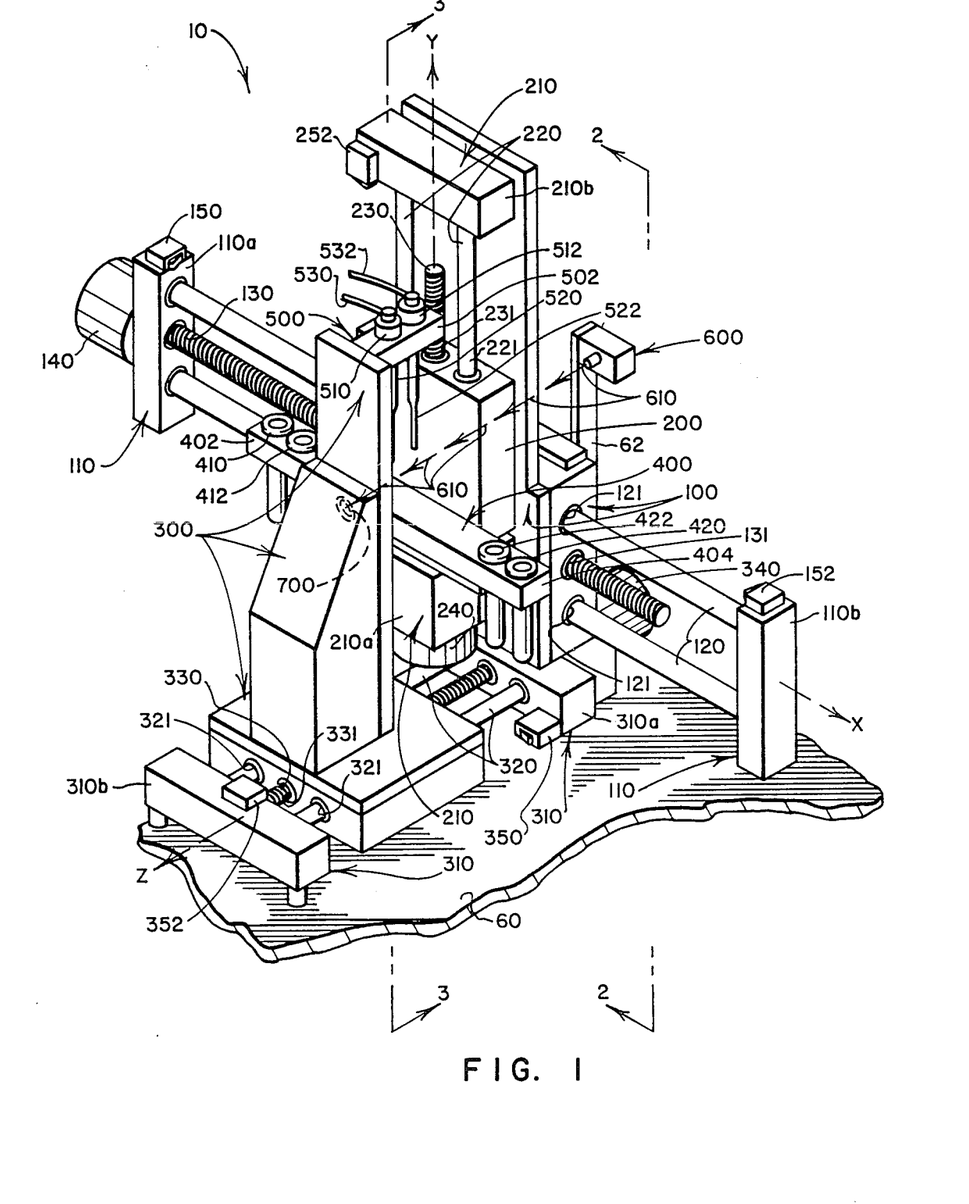

Referring to FIG. 1, an apparatus that embodies features of the preferred practice of the present invention is indicated generally by the numeral 10. The apparatus 10 includes a base plate 60 that extends substantially horizontally. As will be explained, relatively movable components of the apparatus 10 are mounted atop the base plate 60, with various ones of these components being movable leftwardly and rightwardly along what will be referred to as an "X" axis, upwardly and downwardly along what will be referred to as a "Y" axis, and forwardly and rearwardly along what will be referred to as a "Z" axis.

These relatively movable components include a container positioning carriage 100 that is movable relative to the base plate 60 along the X axis, a container positioning sub-carriage 200 that is movable relative to the container positioning carriage 100 along the Y axis, and a pipette positioning carriage 300 that is movable relative to the base plate 60 along the Z axis. For ease of reference, as other elements and features of the apparatus 10 are described, those that extend along, move along, or are otherwise associated with the X axis are designated by three-digit numerals that begin with the digit "1"; likewise, those associated with the Y axis are designated by numerals that begin with "2"; and those associated with the Z axis are designated by numerals that begin with "3".

A container rack 400 is carried by the container positioning sub-carriage 200 which, in turn, is carried by the container positioning carriage 100. By this arrangement, the container rack 400 is movable relative to the base plate 60 along the X and Y axes in conjunction with corresponding X-axis and Y-axis movements of the carriages 100, 200, respectively. The container rack 400 has a left end region 402 that carries a series of four sample containers 410, 412, 414, 416, and a right end region 404 that carries a pair of collection containers 420, 422. For ease of reference, features of the container rack 400 and of the containers carried thereon are designated by three-digit numerals that begin with the digit "4".

A pipette rack 500 is carried by the pipette positioning carriage 300, and is movable relative to the base plate 60 along the Z axis in conjunction with corresponding Z-axis movements of the carriage 300. The pipette rack 500 has a rearwardly extending portion 502 that carries a pair of fittings 510, 512 which support a pair of pipettes 520, 522. Suction hoses 530, 532 couple with the fittings 510, 512 and communicate with the pipettes 520, 522, respectively. For ease of reference, features of the pipette rack 500 and of the pipettes carried thereon are designated by three-digit numerals that begin with the digit "5".

As will be explained, the pipettes 520, 522 are utilized to extract small layered quantities of different fluids from the sample containers 410, 412, 414, 416. The pipette 520 is utilized to withdraw an upper layer of a first type of fluid from each of the sample containers 410, 412, 414, 416 and to deposit the first type of withdrawn fluid in the collection container 420. Likewise, the pipette 522 is utilized to withdraw a lower layer of a second type of fluid from each of the sample containers 410, 412, 414, 416 and to deposit the second type of withdrawn fluid in the collection container 422.

Figure 2:
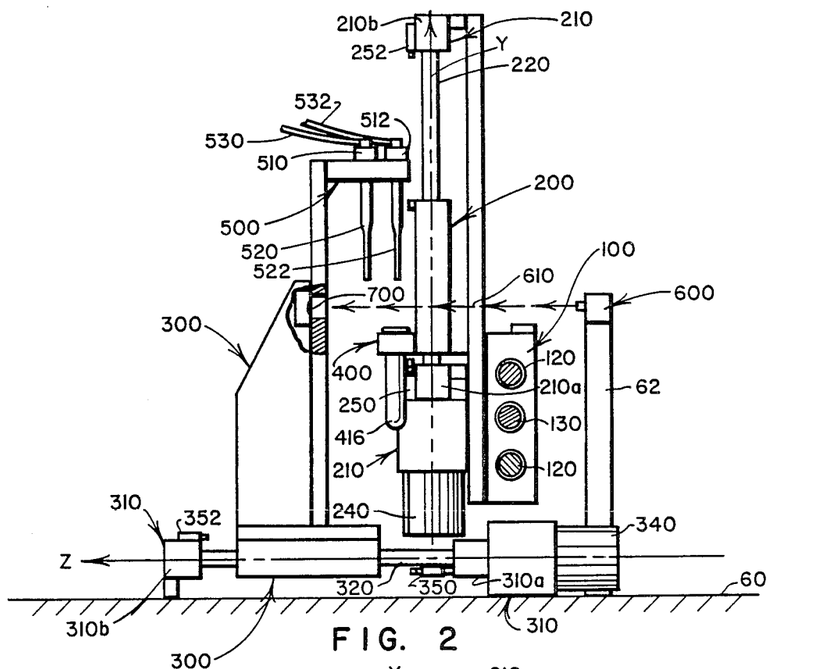
FIGS. 2 and 3 are sectional views as seen from planes indicated by lines 2—2 and 3—3 in FIG. 1.

Referring to FIGS. 1 and 2, a light source 600 is carried by an upwardly extending base structure element 62. The light source 600 is located relatively rearwardly with respect to the Z axis, and serves to project a beam of light forwardly along a path of travel that is indicated by arrows 610. The travel path 610 parallels the Z axis. The beam path 610 crosses the X-axis and the Y-axis ranges of travel of the carriages 100, 200 at about mid points within these ranges of travel. A light sensitive detector 700 is carried by the pipette positioning carriage 300 for receiving light traveling along the beam path 610, and for providing an electrical output signal that is indicative of at least one sensed characteristic of received light, such as its intensity (which, in turn, is indicative of at least one characteristic of the fluid portions that have been interrogated by the light, such as the opacity of the interrogated fluid).

The apparatus 10 is utilized, as will be described in greater detail, to sequentially position the sample containers 410, 412, 414, 416 so that light from the source 600 traveling along the beam path 610 is scanned through the sample containers 410, 412, 414, 416 (and through liquid samples contained therein) to enable the detector 700 to generate electrical output signal values that are stored to provide profiles of the intensity of received light. The signal profiles are utilized to determine the locations within the sample containers 410, 412, 414, 416 of layers of first and second types of liquid that are to be removed by the pipettes 520, 522 and delivered to the collection containers 420, 422, respectively.

Figure 8:
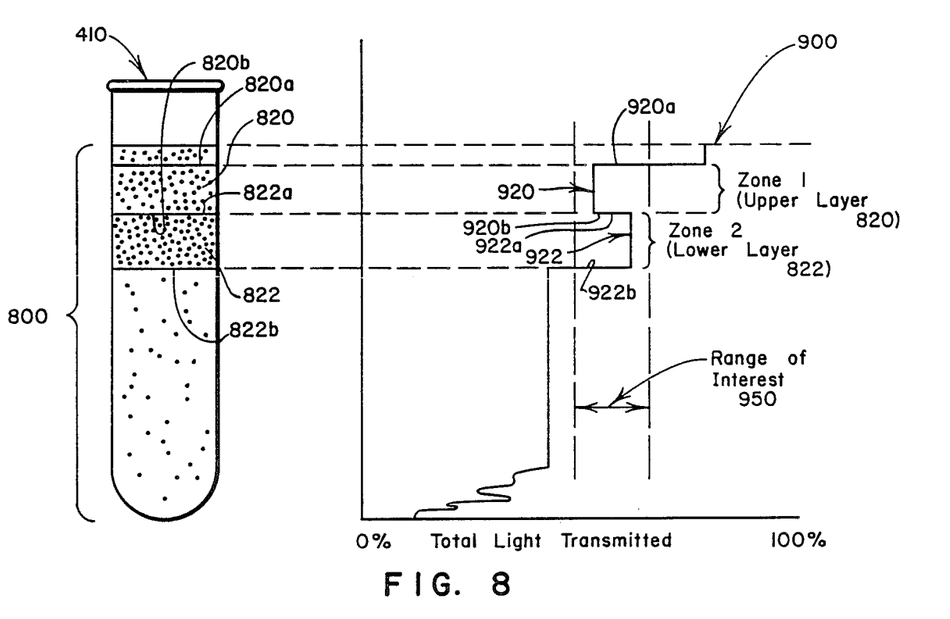

Referring to FIG. 8, a typical one of the sample containers 410 is depicted as containing a layered sample of liquid 800, with spaced upper and lower layers of first and second types of liquid components of interest being indicated by the numerals 820, 822. A graph-like depiction of a profile of sensed output signal values (that are generated by the detector 700 as light from the source 600 is scanned through the sample 800) is indicated by the numeral 900. As is apparent from viewing the profile depicted in FIG. 8, locations of the upper and lower layers 820, 822 are readily ascertained by noting the detected regions 920, 922 wherein the intensities of the light that is transmitted through the layers 820, 822 is found to fall within an "expected" range of values that is indicated by the numeral 950. The expected range (or ranges) can be predetermined by experimentation with samples of the character that are to be used with the apparatus 10, as will be understood by those skilled in the art. The locations of the upper and lower limits 820a, 820b of the upper layer of interest 820 is determined by locating the corresponding graph points 920a, 920b. Likewise, the locations of the upper and lower limits 822a, 822b of the lower layer of interest 822 is determined by locating the corresponding graph points 922a, 922b. The vertical distances between the points 820a, 820b and 822a, 822b are easily discerned from the profile 900, whereby the thicknesses of the layers 820, 822 can be determined with ease from the profile 900. Hence, the volumes of liquid that comprise the layers 820, 822 can be calculated, for the cross-sectional areas of the sample containers 410, 412, 414, 416 are standardized and known.

2. Brief Overview of Operation

A brief overview of the operation of the apparatus 10 will be provided before turning to a more detailed discussion of its construction and operation.

Figures 4, 5:
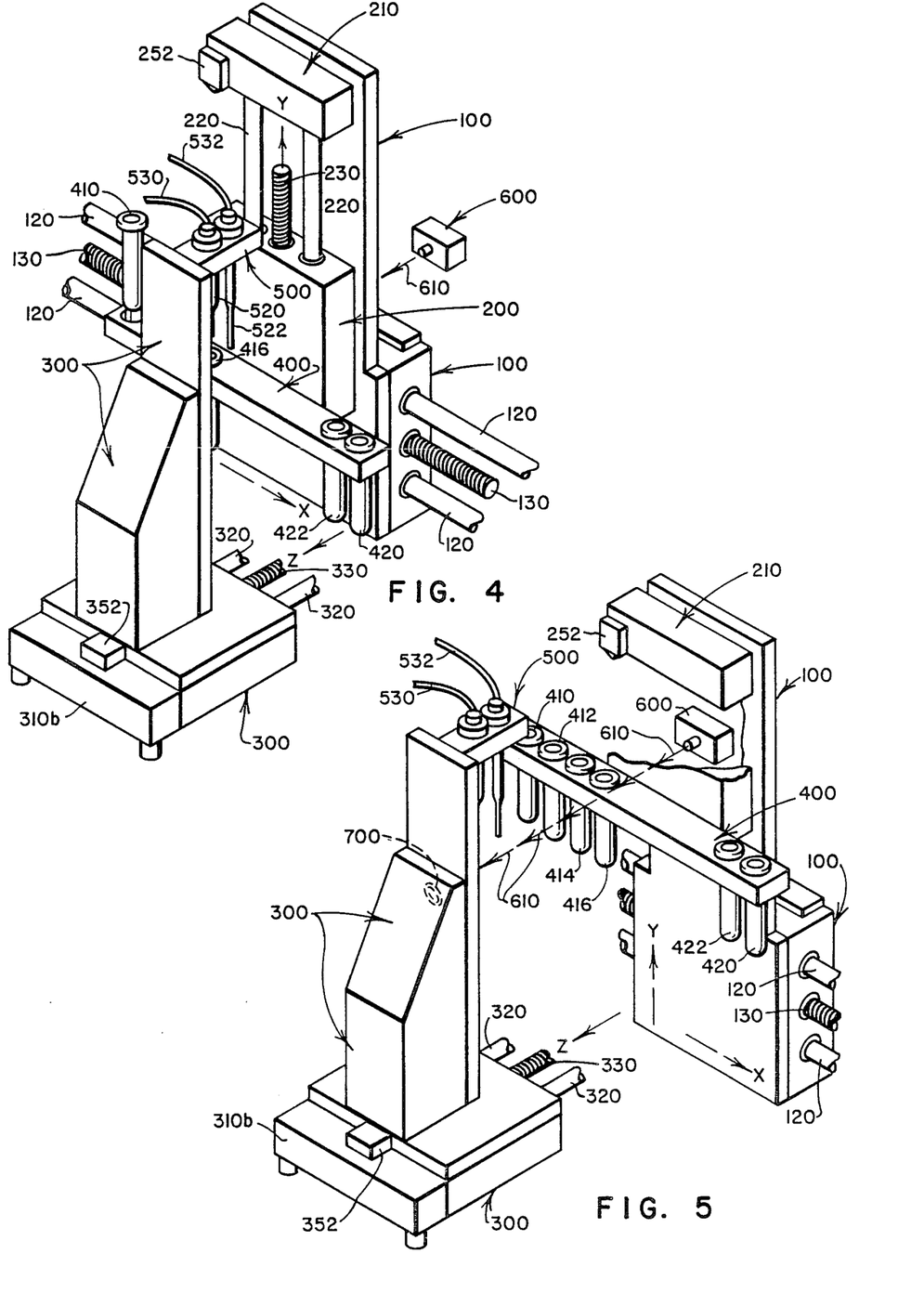
FIGS. 4–7 are perspective views showing selected elements of the apparatus, with relatively movable components being shown in a sequence of positions that are employed during a typical cycle of operation of the apparatus, as will be explained; and, FIG. 8 is a schematic depiction of a test tube containing a typical layered sample of centrifuged liquid, together with a schematic representation of signal values that are sensed during a scan of the sample, with the depicted sample and the associated signal values representing a sample that has two relatively closely spaced layers of interest that contain liquid components which are to be removed from the sample by sequential use of a pair of pipettes that are carried by the pipette positioning stage.

Referring to FIGS. 1, 2 and 4, operation of the apparatus 10 typically is initiated by loading the sample containers 410, 412, 414, 416 and the collection containers 420, 422 into support positions that are defined by the left and right end regions 402, 404 of the container rack 400, and by installing a clean set of the pipettes 520, 522 that will be used to withdraw fluids from the sample containers 410, 412, 414, 416 and to deposit the withdrawn fluids into the collection containers 420, 422. Referring to FIG. 5, scanning of at least one of the sample containers 410, 412, 414, 416 is then effected by orienting the carriages 100, 200 so that the light beam 610 is caused to project through and to vertically scan the contents of the sample containers 410, 412, 414, 416, with the sub-carriage 200 moving the container rack 400 vertically relative to the path 610 of light from the source 600 to effect such scanning. Profiles of output signal values from the detector 700 are stored together with indications of the positions of the light beam travel path 610 relative to the sample container that is being scanned, whereby information is obtained that is indicative of the locations of the first and second zones or layers of interest 820, 822 (see FIG. 8).

The pipette 520 is lowered into the sample containers 410, 412, 414, 416 to the locations within the sample containers 410, 412, 414, 416 of upper layers that contain a first fluid of interest (such as the layer 820 depicted in FIG. 8), and these upper layers of the first fluid are removed by the pipette 520. Likewise, as is typically depicted in FIG. 6, the second pipette 520 is lowered into the sample containers 410, 412, 414, 416 to locations within the sample containers 410, 412, 414, 416 of lower layers of a second fluid of interest (such as the layer 822 depicted in FIG. 8), and these lower layers that contain the second fluid are removed by the second pipette 522.

The pipettes 520, 522 containing their extracted fluids are inserted into the collection containers 420, 422, respectively, to deposit therein the collected quantities of the first and second fluids, respectively. By way of illustration, in FIG. 7, the pipette 522 is shown inserted into the collection container 422 to deposit collected liquid therein.

In the manner described above, the apparatus 10 is operable (1) to ascertain locations of layers of interest within liquid samples, (2) to effect automated pipetting of liquid from these layers to remove such liquid from the samples, and (3) to deposit the extracted fluids in collection containers. All required relative movements of the containers 610, 612, 614, 616, 620, 622, the light beam path 610, and the pipettes 520, 522 is effected by cooperative movements of the carriages 100, 200, 300. Preferably, the various needed movements and other functions of components of the apparatus 10 are automated by providing a conventional microprocessor controller (not shown) that is programmed to execute the required movements and other functions in proper order.

3. Detailed Description

Figure 3:
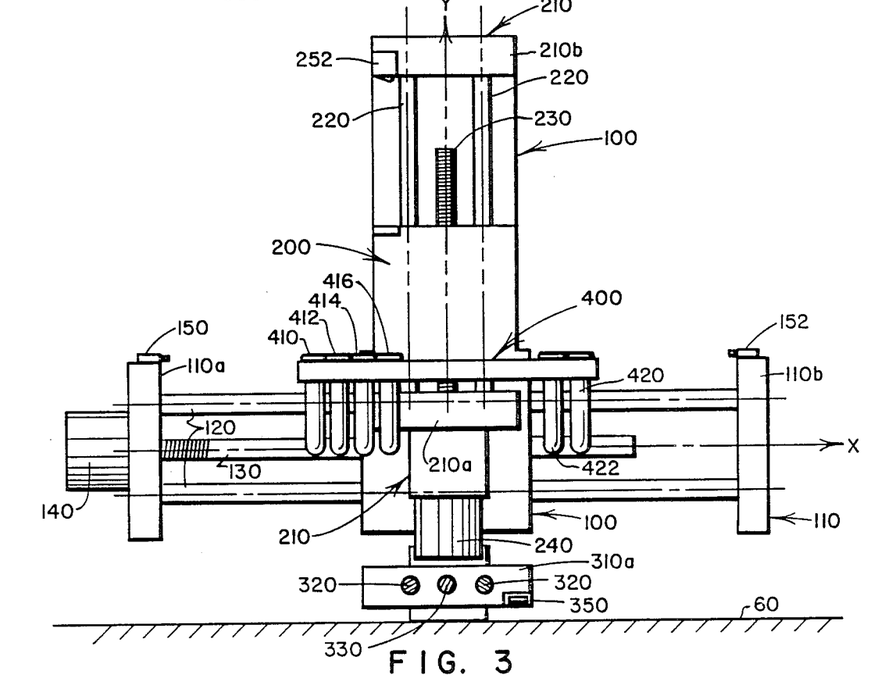

Referring to FIGS. 1-3, two sets of supports 110, 310 are mounted atop the base plate 60. The supports 110, 310 carry pairs of guide rods 120, 320 which extend parallel to the X and Z axes to mount and guide the movements of the carriages 100, 300 along the X and Z axes, respectively. Mounted on the carriage 100 are a set of supports 210 that carry a pair of guide rods 220 which extend parallel to the Y axis to mount and guide movements of the sub-carriage 200 along the Y axis.

The supports 110 include left and right supports 110a, 110b that connect with opposed end regions of a pair upper supports 210a, 210b that connect with opposed end regions of a pair of guide rods 220. The supports 310 include rear and front supports 310a, 310b that connect with opposed end regions of the guide rods 320. The left support 110a, the lower support 210a, and the rear support 310a journal threaded shafts 130, 230, 330 that extend along the X, Y and Z axes at locations centered between the guide rods 120, 220, 320, respectively.

A reversible electric stepping motor 140 is carried by the left support 110a and is drivingly connected to the threaded shaft 130 for rotating the shaft 130. A reversible electric stepping motor 240 is carried by the lower support 210a and is drivingly connected to the threaded shaft 230 for rotating the shaft 230. A reversible electric stepping motor 340 is carried by the rear support 310a and is drivingly connected to the threaded shaft 330 for rotating the shaft 330.

The guide rods 120 extend through aligned openings 121 that are formed in a base portion of the container positioning carriage 100 to guide movements of the container positioning carriage 100 in leftward and rightward directions along the X axis. The threaded shaft 130 extends through a threaded passage 131 that is formed in a base portion of the container positioning carriage 100 and cooperates with the threaded shaft 130 such that, when the motor 140 is operated to rotate the shaft 130, the container positioning carriage 100 will move leftwardly or rightwardly along the guide rods 120 depending on the direction of rotation of the threaded shaft 130 by the motor 140.

The guide rods 220 extend through aligned openings 221 that are formed in the container positioning sub-carriage 200 to guide movements of the carriage 200 in downward and upward directions along the Y axis. The threaded shaft 230 extends through a threaded passage 231 that is formed in the carriage 200 and cooperates with the threaded shaft 230 such that, when the motor 240 is operated to rotate the shaft 230, the carriage 200 will move upwardly or downwardly along the guide rods 220 depending on the direction of rotation of the threaded shaft 230 by the motor 240.

The guide rods 320 extend through aligned openings 321 that are formed in a base portion of the carriage 300 to guide movements of the pipette positioning carriage 300 in forward and rearward directions along the Z axis. The threaded shaft 330 extends through a threaded passage 331 that is formed in a base portion of the pipette positioning carriage 300 and cooperates with the threaded shaft 330 such that, when the motor 340 is operated to rotate the shaft 330, the pipette positioning stage 300 will move forwardly or rearwardly along the guide rods 320 depending on the direction of rotation of the threaded shaft 330 by the motor 340.

Switches 150, 152 are carried by the structures 110 for engaging base portions of the container positioning carriage 100 when the carriage 100 is nearing the ends of its range of travel along the X axis. The switches 150, 152 also serve to provide signals that are used to stop operation of the motor 140 that might otherwise tend to cause undesired movement of the carriage 100 beyond its intended range of movement.

Switches 250, 252 are carried by the structures 210 for engaging base portions of the container positioning sub-carriage 200 when the carriage 200 is nearing the ends of its range of travel along the Y axis. (Switch 250 is shown only in FIG. 2.) The switches 250, 252 also serve to provide signals that are used to stop operation of the motor 240 that might otherwise tend to cause undesired movement of the carriage 200 beyond its intended range of movement.

Switches 350, 352 are carried by the structures 310 for engaging base portions of the pipette positioning carriage 300 when the carriage 300 is nearing the ends of its range of travel along the Z axis. The switches 350, 352 also serve to provide signals that are used to stop operation of the motor 340 that might otherwise tend to cause undesired movement of the carriage 300 beyond its intended range of movement.

The container support rack 400 is affixed to the sub-carriage 200. The rack 400 is an elongate structure that extends substantially horizontally in directions paralleling the X axis, with its left and right end regions 402, 404 projecting leftwardly and rightwardly, respectively, beyond the left and right sides of the sub-carriage 200. The containers 410, 412, 414, 416, 420, 422 are transparent test tubes made of glass or plastics materials of the type that are sufficiently durable to withstand use in a conventional laboratory centrifuge (not shown), with the dimensions of these containers being substantially identical, and with the cross sectional areas of these containers being known. Mounting positions are defined in the left and right end regions 402, 404 for snugly receiving the containers 410, 412, 414, 416, 420, 422 so that when these containers are inserted into the rack 400, the rack 400 will function to securely support these containers in vertically extending orientations.

The pipette support rack 500 is affixed to the pipette positioning carriage 300. The rack 500 is an elongate structure that extends substantially horizontally in directions paralleling the Z axis, with its rearward end region carrying connectors 510, 512 that serve to support the pipettes 520, 522, and to communicate the pipettes 520, 522 with the suction hoses 530, 532, respectively. The connectors 510, 512 are commercially available connectors that are designed to establish hose-to-pipette connections, and to mount the pipettes 520, 522 in vertically extending orientations.

Because the pipettes 520, 522 are of a standard, uniform dimensions and have known, uniform lengths, the connectors 510, 512 function to support the pipettes 520, 522 such that tip portions 540, 542 of the pipettes 520, 522 are positioned at an identical distances beneath the pipette support rack 500. By this arrangement, it is not necessary to sense or check the actual locations of the tip portions 540, 542 at any time during the entire cycle of operation of the apparatus 10. If desired, however, or if pipettes 520, 522 of non-uniform (i.e., unknown) lengths are to be used, the cycle of operation of the apparatus 10 can be modified to include a procedure for optically checking the locations of the lower tip portions 540, 542 of the pipettes 520, 522 so that the actual locations of the tip portions 540, 542 relative to the support 500 will at all times be known and so that mis-positioning of the tip portions 540, 542 of the pipettes 520, 522 within the containers 410, 412, 414, 416 is minimized. By this arrangement, the precision of the apparatus 10 in effecting a very exacting removal of even extremely thin layers of liquid from the sample containers 410, 412, 414, 416 is maximized.

In preferred practice, the motors 140, 240, 340 that are utilized to effect relative X, Y and Z axis movements of the carriages 100, 200, 300, respectively, are D.C. stepping motors that cause the shafts 130, 230, 330 to rotate in small, distinct increments of motion or "steps." Relative locations of the carriages 100, 200, 300 are ascertainable (i.e., "known") by monitoring the number of increments of motion or "steps" that have been executed by the motors 140, 240, 340. As will be understood by those skilled in the art, the pairs of limit switches 150/152, 250/252, 350/352 that are provided as safety devices (to assure that relative movements of the carriages 100, 200, 300 along the guide rods 120, 220, 320 do not tend to exceed the desired X-, Y- and Z-axis ranges of travel) also may be used to check the accuracy of calculated positions of the carriages 100, 200, 300; however, in preferred practice it is more accurate (and therefore more desirable) to use optical sensors (not shown) that cause optical beams to be interrupted by the carriages 100, 200, 300 as the carriages 100, 200, 300 move past known points along their paths of travel (with such position checks being made at least as often as each time when operation of the apparatus 10 is being initiated).

Control of the suction action that is effected by the pipettes 520, 522 to withdraw selected quantities of liquid from samples within the sample containers 410, 412, 414, 416 is governed at least in part by the detected features of the profiles of the various layers of fluid within the sample containers 410, 412, 414, 416 that have been interrogated by the light beam 610. Preferably a microprocessor system controls the suction action so that the vigor with which it is carried out is controlled in accordance with the volume and character of the sample portions that are to be extracted (e.g., a gentle, slow suction action is preferably used with very small sample portions that are to be extracted so that liquid that is located outside the region of interest is not drawn into a pipette). A typical profile 900 of signal values generated by the detector 700 during a scan by the light beam 610 of one of the sample containers 410, 412, 414, 416 is depicted in FIG. 8.

Because the dimensions of the sample containers 410, 412, 414, 416 are known (i.e., the cross sectional areas of the sample containers 410, 412, 414, 416 are standardized and known in advance of use of these containers), and because the profile 900 as depicted in FIG. 8 provides a very exact indication of the thickness of sample layers 820, 822 of interest, the volumes of liquid that comprises the sample layers 820, 822 which are to be removed by use of the pipettes 520, 522 can be calculated before use of the pipettes 520, 522 is initiated. Therefore, the extent to which suction action is needed to effect removal of desired sample layers by the pipettes 520, 522 is determined in advance, and the exact degrees of required suction action are applied to the pipettes 520, 522 by the hoses 530, 532 to effect extractions from the samples of the desired volumes of fluid. Because automated pipetting apparatus for removing known volumes of liquid from a sample utilizing controlled suction applied to a pipette are well known and long have been commercially available, such apparatus is not depicted in the drawings and need not be described here.

While control of the positioning of the various relatively movable components of the apparatus 10 (e.g., the carriages 100, 200, 300) can be effected manually as by physically observing the positioning of these relatively movable components and individually operating the stepping motors 140, 240, 340 to cycle the carriages 100, 200, 300 through their various needed movements, preferred practice calls for the motors 140, 240, 340 to be operated in response to control signals that are provided under the control of a conventional, commercially available microprocessor (not shown) that is suitably programmed (1) to utilize signals from the switches 150, 152, 250, 252, 350, 352, (2) to keep track of the number of pulses applied to the stepping motors 140, 240, 340, (3) to effect the desired types of movements so that scanning of the sample containers 410, 412, 414, 416 is achieved and sensed profiles are obtained from interrogated samples as has been described, and (4) to effect pipetting and collection of liquid from layers of fluid within the sample containers 410, 412, 414, 416 as a function of the sensed locations and thicknesses of these layers of liquid.

Because the pipettes 520, 522 have outer diameters that are ordinarily substantially less than the inner diameters of the sample containers 410, 412, 414, 416, usually it is possible to move the pipettes 520, 522 about within the sample containers 410, 412, 414, 416 (i.e., to effect movement of the pipettes 520, 522 toward and away from interior wall surfaces of the sample containers 410, 412, 414, 416) such that the tips 540, 542 of the pipettes 520, 522 are caused to travel in generally circular movements relative to the sample containers 410, 412, 414, 416 (with the tips 540, 542 of the pipettes 520, 522 being maintained in a substantially horizontal plane during said movement) and to thereby facilitate removal of liquid from a horizontal layer so as to better implement the desired objective of effecting a thorough removal of components from within the sample containers 410, 412, 414, 416. Usually such movement of the pipettes 520, 522 relative to the containers 410, 412, 414, 416 is not necessary in order to effect thorough extractions of layers of liquid from the samples; however, if such relative movements are desired, they can be effected by operating the motors 140, 340 in conjunction with each other such that the needed left and right relative movements of the container positioning carriage 100 is combined with the needed forward and rearward relative movements of the pipette positioning carriage 300 to achieve the desired types of relative circular movements between the tips 540, 542 of the pipettes 520, 522 and the sample containers 410, 412, 414, 416.

The incremental nature of the vertical movement of the rack 400 that takes place during a scanning operation (wherein the light beam 610 is used to interrogate the contents of one of the containers 410, 412, 414, 416) is desirable in that readings of light intensity that are taken intermittently by the light sensitive detector 700 are taken at times when the rack 400 is stationary, i.e., at a fixed, known position. Thus, the light intensity readings that are taken by the detector 700 represents exact readings taken at exact known positions of the light beam 610 intercepting a sample container that is being interrogated.

While the light source 600 is preferably a collimated beam of polarized laser light, other sources of light may be utilized if tests indicate that the character of the light that is transmitted through the samples being interrogated is suitably affected by appropriate characteristics of the samples.

While the light sensitive detector 700 is preferably a photodiode, other types of light sensitive detectors may be utilized if tests indicate that the detectors function properly to sense changes in characteristics of light from the source 600 that has been transmitted through the samples to be interrogated.

4. Operational Description

In one application for which the apparatus 10 is well suited, centrifuged test tubes of liquid samples of blood are optically interrogated to locate and remove from within the samples very thin layers of liquid constituents that are of interest for testing, for making serum, or for other purposes.

Operation of the apparatus 10 typically is initiated by loading the sample containers 410, 412, 414, 416 and the collection containers 420, 422 into support positions that are defined by the left and right end regions 402, 404 of the container rack 400 as is depicted in FIGS. 1-3, and by installing a clean set of the pipettes 520, 522 that will be used to extract fluids from the sample containers 410, 412, 414, 416 and delivering the extracted fluid to the collection containers 420, 422. If the pipettes 520, 522 are not of a standard or known length, then the location of the pipette tips 540, 542 relative to the pipette support rack 500 is determined, preferably by using a conventional optical sensor (not shown). Scanning of the sample containers 410, 412, 414, 416 is then effected (as is typically illustrated in FIG. 5) by orienting the carriages 100, 200, 300 so that the light beam 610 is caused to project through and to vertically scan the contents of the sample containers 410, 412, 414, 416.

In positioning the sample containers 410, 412, 414, 416 relative to the light beam path 610 for optimum scanning, an optional procedure can be utilized to assure that each of the containers 410, 412, 414, 416 is properly aligned with the beam path 610 so that light from the source 600 will pass through a maximum quantity of the samples being interrogated, and so that light being transmitted through walls of the containers 410, 412, 414, 416 is subjected to as little refraction as possible by the walls of these containers. Horizontal centering of the containers 410, 412, 414, 416 with respect to the beam path 610 preferably is effected by conducting horizontal scans of the containers 410, 412, 414, 416 to locate what will be referred to as the optical centers of the containers 410, 412, 414, 416. As these horizontal scans are conducted, output from the detector 700 is monitored to detect optimum relative locations of the containers 410, 412, 414, 416 and the beam path 610 that produce maximum light transmission, whereupon these relative locations are utilized during the vertical scans that are made of the containers 410, 412, 414, 416 to detect for variations in transmitted light that are indicative of changes in the makeup of the samples at various levels within the containers 410, 412, 414, 416.

Vertical scanning of the containers 410, 412, 414, 416 by the beam 610 is effected by slowly pulsing the stepping motor 240 to move the container positioning sub carriage 200 vertically in distinct increments of motion. During each step, a sensor reading from the detector 700 is recorded, with each of these readings being labeled with respect to the relative position of the container being interrogated when the reading was taken. The compilation of these readings forms a profile of the type indicated by the numeral 900 in FIG. 8.

For each type of sample that is to be scanned and separated, it is desirable that a microprocessor system be utilized to compare collected data from each sample with a data set that represents an ideal model sample (which has been created by human effort in operating the machine in a manual mode—whereafter numerous samples have been automatically collected and compared with the created model data so that the propriety of the model sample data can be improved to provide ideal model sample data, with the cycle of testing and refinement of the model data being repeated to the degree desired to progressively enhance the ideal model sample data). With the data from the scans of actual samples to be analyzed and separated being continually monitored and checked either by a microcomputer system or by human endeavor, valid means of comparison can be developed to enable reliable automated determinations to be effected with respect to how the stepping motors 140, 240, 340 should be operated to move the carriages 100, 200, 300 to appropriately effect relative positionings of the container rack 400 and the pipette rack 500 (i.e., the sample containers 410, 412, 414, 416, the collection containers 420, 422, and the pipettes 520, 522) to lower the pipettes 520, 522 into the samples to effect removal of desired quantities of liquid from sample layers of interest, which are designated by the numerals 820, 822 in FIG. 8.

Figures 6, 7:
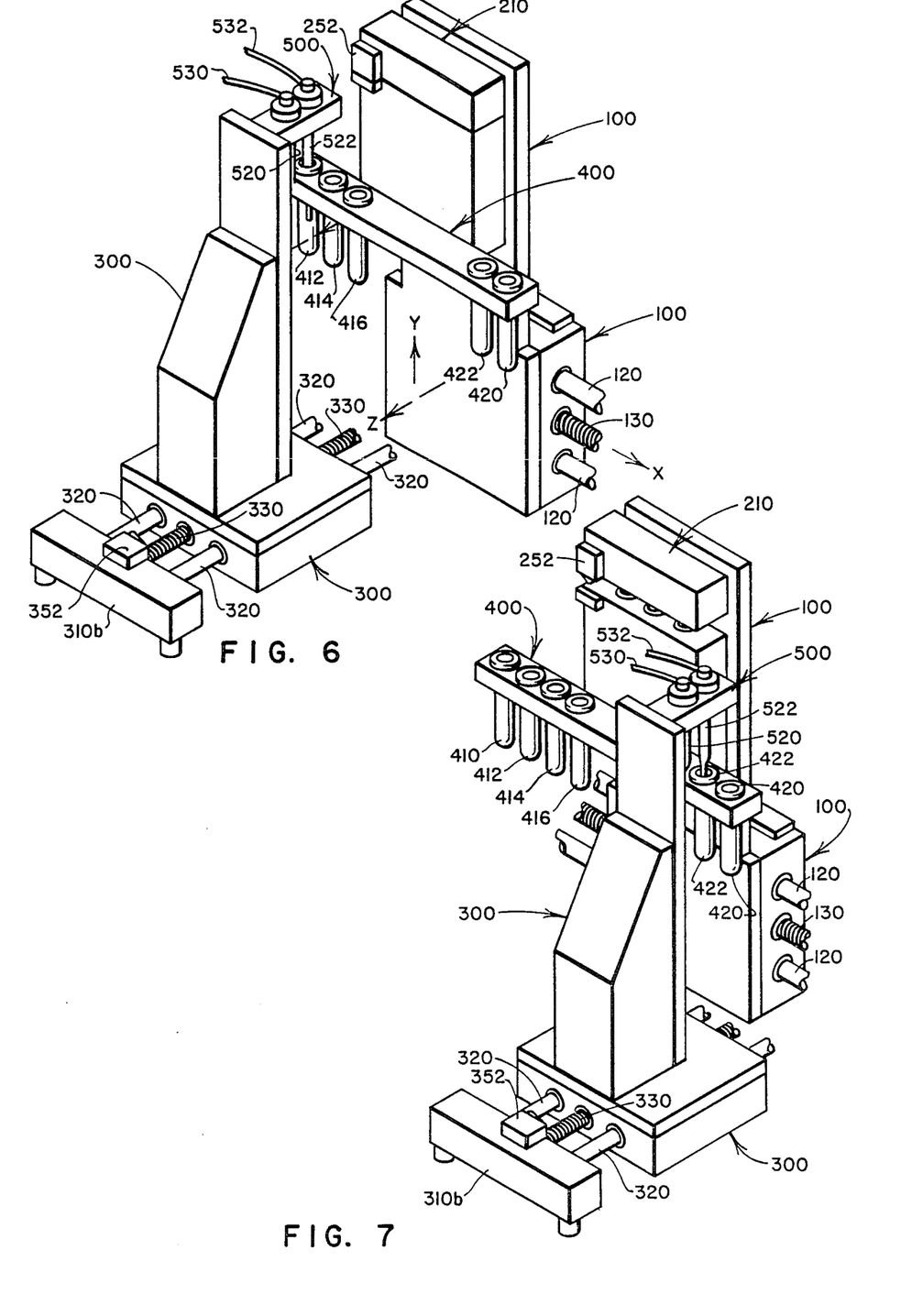

During the pipetting operation, the pipette 520 is lowered into the sample containers 410, 412, 414, 416 to the locations within the sample containers 410, 412, 414, 416 where upper layers 820 that contain a first fluid are found, and these upper layers of the first fluid are removed by the pipette 520. Likewise, as is typically depicted in FIG. 6, the second pipette 520 is lowered into the sample containers 410, 412, 414, 416 to the locations within the sample containers 410, 412, 414, 416 where lower layers 822 of a second fluid of interest are found, and these lower layers that contain the second fluid are removed by the second pipette 522. The pipettes 520, 522 are inserted into the collection containers 420, 422, respectively, to deposit therein the collected quantities of the first and second fluids, respectively. In FIG. 7, the pipette 522 is shown inserted into the collection container 422 to deposit collected liquid therein.

5. Conclusion

While the foregoing discussion of the preferred embodiment and the accompanying drawings disclose an apparatus 10 that is designed to accommodate only four sample containers 410, 412, 414, 416 and only two collection containers 420, 422, and while the described embodiment utilizes only two pipettes 520, 522 to extract liquid samples, it will be understood that principles of the present invention are not confined to use with an apparatus that is so limited in the number of containers and pipettes that it can accommodate. It is quite within the scope of practice of the invention to utilize an apparatus (not shown) that can accommodate, in sequence, a much larger supply of sample containers, that can collect more than two types of liquid constituents from interrogated samples, and that uses a relatively large number of pipettes to enhance efficiency of operation. Likewise, the system of the present invention can be utilized to extract and separately collect different fluid components from a plurality of fluid samples, with each extracted component being delivered to a separate collection container (i.e., without extracted components from different fluid samples being combined in common collection containers).

While a basically linear arrangement of sample containers and collection containers has been described and illustrated, it is possible to use nonlinear arrangements such as a semicircular arrangement of these containers, with the semicircular arrangement of containers being moved in an arcuate or circular path of travel so that scanning can be effected at one station along the path, and fluid extraction and collection can be effected at another station or stations along the path, which arrangement is not illustrated herein inasmuch as it is simply typical of a number of other arrangements that can be utilized, as will be apparent to those skilled in the art. Likewise relative movements of various components of the described system are not limited to an orthogonal arrangement of X-, Y-, and Z-axes, but rather can include or be supplanted by an arrangement of radial, axial and circumferential movements about an imaginary center axis. Still further, the positioning of pipettes within sample containers to collect fluid from layers of interest can utilize any of a variety of movements of the pipette tip relative to the container to facilitate achieving a thorough extraction of fluid from the layers of interest For special applications where there are a large number of articles that are suspended with a sample, it is possible to sense the light that is scattered by the sample, with the sensor being placed, for example, at an orientation which is intended to detect light that is scattered by the particles and deflected from the incident beam path by about ninety degrees. It is anticipated that systems which use circular path movement of samples, and that employ detectors to sense scattered light rather than transmitted light—and yet which embody much of the spirit of the system of the present invention—will be made the subject of at least one continuation-in-part application as prototypes are developed and tested.

Whereas the described embodiment of the present invention utilizes pipettes that are of a consistent and known length in order for the position of the tips of the pipettes to be known and relied on for proper positioning of the tips to collect fluid from layers of interest within samples, it is expected that a next generation of apparatus that embodies the system of the present will likely include optical sensing systems to check for and ascertain the exact positions of the tips of the pipettes so that pipettes of varying lengths can be used with no decrease in operating efficiency or in sample collection reliability. These and other modifications of the described embodiment can be made without departing from the spirit and scope of the invention, a will be apparent to those skilled in the art.

While the foregoing discussion of the preferred embodiment has utilized terms such as leftward, rightward, upward, downward, forward, rearward, etc., in describing relative directions, orientations, positions and movements, etc., it will be understood that such terms are used simply to facilitate a clear understanding of the described embodiment, and are not intended to be limiting in scope. Clearly, principles of the invention are usable with components and elements that are oriented, positioned, and/or moved differently than has been described, and that execute other forms of relative movement.

Although the invention has been described in its preferred form with a certain degree of particularity, it will be understood that the present disclosure of the preferred form has been made only by way of example, and that numerous changes in the details of construction and the combination and arrangements of parts and the like may be resorted to without departing from the spirit and scope of the invention as hereinafter claimed. By way of but one example, the motors 140, 240, 340 that effect relative movements of the described components of the apparatus 10 can be repositioned and/or can be indirectly connected using conventional drive train components to the described components that are driven by the motors 140, 240, 340. Accordingly, it is intended that the patent shall cover, by suitable expression in the appended claims, whatever features of patentable novelty exist in the invention disclosed.

What is claimed is:

1. A method for interrogating a sample of liquid to locate at any vertical location within the sample a region of interest in the form of a layer of liquid of substantially an degree of thinness to as low as on the order of 10–50 microns that has top and bottom surfaces that extend substantially horizontally, and to withdraw and collect liquid from the region of interest, wherein the sample is of a type that has at least one light influencing characteristic that varies from position to position within the sample, including the steps of:
    (a) projecting a beam of collimated, polarized light from a laser along a substantially horizontal path of travel;
    (b) arranging the relative positions of said path of travel and of the sample of liquid so that the beam of light intercepts selected portions of the sample of liquid as the beam is projected along said path of travel;
    (c) arranging the relative positions of said path of travel, the sample of liquid, and a light sensitive detector means to cause the detector means to receive light from the beam that has been transmitted substantially in a straight line path through said selected sample portions;
    (d) effecting relative movement of the sample with respect to said path of travel and the detector means, to cause scanning by the beam of light of said selected sample portions, with light from the beam that has been transmitted through said selected sample portions that have been scanned by the beam of light (referred to hereinafter as "said scanned sample portions") being received by the detector means.
    (e) Operating the detector means to sense received light from said scanned sample portions and to generate an electrical output signal that has a value which is representative of at least one sense characteristic of the received light, with variations in values of the output signal being representative of variations from position to position within said scanned sample portions of at least one transmitted light influencing characteristic of the sample, and to coordinate output signal values with indications of corresponding positions within the sample, to thereby locate within said scanned sample portions at least one region of interest;
    (f) providing liquid withdrawal means for insertion into the sample, with the liquid withdrawal means having structure defining an inlet opening for withdrawing liquid from the sample through the inlet opening;
    (g) effecting relative movement of the sample of liquid and the liquid withdrawal means to insert the liquid withdrawal means into the sample of liquid to position the inlet opening thereof substantially at any desired vertical location in the sample in communication with liquid within the layer that forms said region of interest;
    (h) operating the liquid withdrawal means to effect withdrawal of liquid from within the layer that forms said region of interest through the inlet opening and to collect the withdrawn liquid; and,
    (i) wherein the step of effecting positioning of the sample includes the steps of:
        (i) providing the sample in an elongate, vertically extending test tube formed of substantially transparent material such as glass, with the test tube defining an interior of substantially circular cross section wherein the sample is carried; and,
        (ii) moving the test tube containing the sample in a substantially horizontal direction that extends transverse to said path of travel of the light beam to be transmitted through a layer of the sample while operating the detector means to locate the optimum relative positioning of the test tube and said path of travel of the light beam that maximizes the light transmission through the sample, whereby the test tube is caused to be horizontally centered with resect to the travel path of the beam.

2. A method for interrogating a sample of liquid to locate a region of interest within the sample, and to withdraw and collect liquid from the region of interest, wherein the sample is of a type that has at least one light influencing characteristic that varies from position to position within the sample, including the steps of:

(a) providing base means including a base structure with supports thereon defining substantially orthogonally oriented paths of movement extending along imaginary lines that are perpendicular to each other, these lines being referred to as an "X axis" and a "Z axis";

(b) providing container positioning carriage means connected to said supports for movement along the X axis;

(c) providing the container positioning carriage means with support structure thereon defining a path of movement extending along an imaginary line referred to as the "Y axis", with the Y axis extending substantially perpendicular to each of the X axis and the Z axis;

(d) providing container positioning sub-carriage means connected to the support structure for movement relative thereto along the Y axis;

(e) providing container support means connected to the container positioning sub-carriage means for movement with the container positioning carriage means along the X axis, and for movement with the container positioning sub-carriage means along the y axis;

(f) providing pipette positioning carriage means connected to said supports for movement along the Z axis; (g) providing pipette support means connected to the pipette positioning carriage means for movement therewith along the Z axis;

(h) providing a source of light connected to the base means for support;

(i) operating the source of light to project a beam of light along a path of travel;

(j) supporting the sample of liquid in a container that is connected to the container support means for movement therewith along the X and Y axes to position the sample so that selected portions of the sample intercept the path of travel of the light beam;

(k) providing a light sensitive detector means connected to the pipette position carriage for support, and positioned to receive light that has been transmitted from the source along the beam path and intercepted by the selected sample portions;

(l) moving at least one of said carriage means and said sub-carriage means to effect relative movement of the sample with respect to the path of travel of the light beam and the detector means, to cause scanning by the beam of light of said selected sample portions with light from the beam that has been intercepted by said selected sample portions which have been scanned by the light beam (referred to hereinafter as "said scanned sample portions") being received by the detector means;

(m) operating the detector means to sense received light from said scanned sample portions and to generate an electrical output signal that has a value which is representative of at least one sensed characteristic of the received light, with variations in values of the output signal being representative of variations from position to position within said scanned sample portions of at least one light influencing characteristic of the sample, and to coordinate output signal values with indications of corresponding positions within the sample, to thereby locate within said scanned sample portions at least one region of interest;

(n) providing liquid withdrawal means for insertion into the sample, with the liquid withdrawal means having structure defining an inlet opening for withdrawing liquid from the sample through the inlet opening:

(o) effecting relative movement of the sample of liquid and the liquid withdrawal means to insert the liquid withdrawal means into the sample of liquid to position the inlet opening in communication with said region of interest;

(p) operating the liquid withdrawal means to effect withdrawal of liquid through the inlet opening from said region of interest and to collect the withdrawn liquid;

(q) with the step of moving at least one of said carriage means and said subcarriage means to effect relative movement of the sample including the step of supporting the sample within an elongate open-ended container, with the container having a substantially ring-like side wall that defines a generally circular cross section of a substantially uniform inner diameter;

(r) with the stop of providing liquid withdrawal means including the step of providing a pipette for insertion into the open-ended container, with the pipette having an outer diameter that is substantially less than the inner diameter of the open-ended container, and with the pipette having a tip that defines an inlet opening for withdrawing liquid from the container; and, (s) with the step of operating the liquid withdrawal means including the step of effecting a relatively circular movement of the pipette about within the container during withdrawal of liquid from the container, with the tip of the pipette being maintained in a substantially horizontal plane during said movement, whereby removal of a liquid from within a horizontal layer within the container is facilitate.

3. A method for interrogating a sample of liquid to detect how at least one characteristic of the makeup of the sample varies from position to position within selected portions of the sample, including the steps of:

(a) projecting a beam of light along a predetermined path of travel;

(b) positioning the sample of liquid so that the beam of light intercepts selected portions of the sample as the beam is projected along said path of travel;

(c) positioning light sensitive detector means to receive light from the beam that has been transmitted through said selected portions of the sample;

(d) effecting relative movement of the sample and said path of travel to cause scanning by the beam of light of said selected portions of the sample;

(e) operating the detector means to receive light that has been transmitted through said selected portions of the sample and to sense values of the received light, with variations in the sensed values being representative of variations from position to position within said selected portions of the sample of at least one characteristic of the makeup of the sample, and with the senses values serving to indicate a location within said selected portions of the sample of a region of interest;

(f) recording said sensed values together with values that are indicative of locations within the liquid sample that correspond to said sensed values to form a record, whereby the location of the region of interest within the sample is indicated by the recorded values of the record;

(g) with the step of projecting a beam including the step of projecting a beam of light along a substantially horizontal travel path; and, (h) with the step of positioning the sample including the steps of:

(i) providing the sample in an elongate, vertically extending test tube formed of substantially transparent material such as glass, with the test tube defining an interior of substantially circular cross section wherein the sample is carried; and, (ii) moving the test tube containing the sample in a substantially horizontal direction that extends transverse to said path of travel of the light beam to cause the light beam to be transmitted through a layer of the sample while operating the detector means to locate the optimum relative positioning of the test tube and said path of travel of the light beam that maximizes the light transmission through the sample, whereby the test tube is caused to be horizontally centered with respect to the travel path of the beam.

4. Apparatus for interrogating a sample of liquid to locate a region of interest within the sample, and to withdraw and collect liquid from the region of interest, wherein the sample is of a type that has at least one light influencing characteristic that varies from position to position within the sample, the apparatus comprising:

(a) light source means for projecting a beam of light along a predetermined path of travel;

(b) sample support means for positioning the sample of liquid so that the beam of light intercepts selected portions of the sample as the beam is projected by the light source means along said path of travel, wherein the sample support means includes elongate container means formed from substantially transparent material such as glass, and the container means extends vertically and contains the sample of liquid during interrogation of the sample of liquid by the light beam;

(c) positioning means connected to at least one of the light source means and the sample support means for effecting relative movement of the sample and the path of travel of the beam of light that is projected from the light source means to cause scanning by the beam of light of said sample portions;

(d) light sensitive detector means for receiving light from the beam that has been transmitted through said sample portions during said scanning and for sensing at least one characteristic of the received light, that varies from position to position within the selected portions of the sample, and for generating an output signal that is representative of the sensed characteristics, with variations in the output signal serving to indicate a location within the selected sample portions of a region of interest;

(e) withdrawal means for insertion into the sample, with the withdrawal means having structure defining an inlet opening for withdrawing liquid from the sample through the inlet opening and defining a chamber that communicates with the inlet opening for receiving and collecting withdrawn liquid;

(f) said positioning means additionally being functional for effecting insertion of the withdrawal means into the liquid sample and to position the inlet opening thereof within said region of interest to enable the withdrawal means to effect withdrawal of liquid through the inlet opening from said region of interest and to collect the withdrawn liquid;

(g) the container means having a substantially uniform cross section along at least a majority of its length; and, (h) the positioning means, the light source, and the detector means being operable to effect horizontal centering of the container means relative to the travel path by moving the container means and the liquid sample carried therein in a substantially horizontal direction that extends transverse to said path of travel of the light beam to cause the light beam to be transmitted through a layer of the sample while operating the detector means to locate the optimum relative positioning of the container means and said path of travel of the light beam that maximizes the light transmission through the sample, whereby the container means is caused to be horizontally centered with respect to the travel path of the beam.

5. An apparatus for non-contact scanning a liquid sample that contains within it a plurality of distinct layers of liquid, wherein at least one of the layers contains primarily a concentration of a liquid constituent that differs from the content of an adjacent layer, with the apparatus having a capability to locate said at least one of the layers as by non-contact scanning of the sample, and having a capability to remove liquid from said at least one of the layers, the apparatus comprising:

(a) structure defining base means;

(b) sample container means connected to the base means for receiving and containing a sample of liquid with the sample having a plurality of distinct layers of liquid, wherein at least one of the layers contains primarily a concentration of a liquid constituent that differs from the content of an adjacent layer, and with the sample container means being substantially transparent to light such that light can be projected in the form of a beam through the liquid sample contained within the sample container means to interrogate the liquid sample;

(c) light source means connected to the base means for emitting a beam of light along a path of travel for transmission through at least a portion of the sample container means toward the liquid sample contained within the sample container means;

(d) light sensitive detector means connected to the base means for receiving light from the beam that has been projected toward the sample and has been influenced by the sample, and for generating a signal having a value that is indicative of the influence the sample has had on such received light;

(e) positioning means connected to the base means for effecting relative movement of the sample with respect to at least a selected one of the light source means and the detector means for causing light that is received by the detector means to be representative of a scan through selected portions of the sample, with the selected portions of the sample that have been scanned extending through at least one of a plurality of distinct layers of liquid that comprise the sample, wherein said at least one of the layers contains primarily a concentration of a liquid constituent that differs in detected light characteristics from the content of an adjacent layer, whereby the value of the signal is caused to vary in accordance with the manner in which received light has been influenced by scanned selected portions of the sample, with the presence within the scanned sample portions of a layer of interest being identified;

(f) liquid withdrawal means connected to the base means for insertion into the sample for removing a desired quantity of liquid from said layer of interest;

(g) with the sample container means including an elongate container formed from substantially transparent material such as glass, and the container means extends vertically and contains the sample of liquid during interrogation of the sample of liquid by the light beam;

(h) with the positioning means being operable to effect a vertical scan of said sample portions;

(i) with the container means having a substantially uniform cross section along at least a majority of its length; and, (j) with the positioning means, the light source means, and the detector means being operable to effect horizontal centering of the container means relative to the travel path by moving the container means and the liquid sample carried therein in a substantially horizontal direction that extends transverse to said path of travel of the light beam to cause the light beam to be transmitted through a layer of the sample while operating the detector means to locate the optimum relative positioning of the container means and said path of travel of the light beam that maximizes the light transmission through the sample, whereby the container means is caused to be horizontally centered with respect to the travel path of the beam.

* * * * *